(12) United States Patent
Fan

(10) Patent No.: US 10,420,780 B2
(45) Date of Patent: Sep. 24, 2019

(54) 25-HYDROXY VITAMIN D3 COMPLEX AND METHODS OF MANUFACTURE AND ITS APPLICATIONS

(71) Applicant: RCC CORPORATION LIMITED, Nanjing, Jiangsu (CN)

(72) Inventor: Haiyan Fan, Jiangsu (CN)

(73) Assignee: RCC CORPORATION LIMITED, Nanjing, Jiangsu (CN)

( * ) Notice: Subject to any disclaimer, the term of this patent is extended or adjusted under 35 U.S.C. 154(b) by 0 days.

(21) Appl. No.: 15/667,685

(22) Filed: Aug. 3, 2017

(65) Prior Publication Data

US 2018/0325922 A1 Nov. 15, 2018

(30) Foreign Application Priority Data

May 15, 2017 (CN) .......................... 2017 1 0338735

(51) Int. Cl.
| | | |
|---|---|---|
| A23K 20/163 | (2016.01) | |
| A61K 31/593 | (2006.01) | |
| A23K 20/174 | (2016.01) | |
| A61K 47/40 | (2006.01) | |
| A23K 50/75 | (2016.01) | |
| A61K 47/69 | (2017.01) | |
| A61K 9/51 | (2006.01) | |
| A23L 5/00 | (2016.01) | |

(52) U.S. Cl.
CPC .......... *A61K 31/593* (2013.01); *A23K 20/163* (2016.05); *A23K 20/174* (2016.05); *A23K 50/75* (2016.05); *A23L 5/00* (2016.08); *A61K 9/5161* (2013.01); *A61K 47/40* (2013.01); *A61K 47/6951* (2017.08); *A23V 2002/00* (2013.01)

(58) Field of Classification Search
None
See application file for complete search history.

(56) References Cited

U.S. PATENT DOCUMENTS

| | | | |
|---|---|---|---|
| 2005/0276841 A1* | 12/2005 | Davis ................... | A61K 9/0051 424/443 |
| 2007/0093448 A1* | 4/2007 | Westermann ............ | B82Y 5/00 514/58 |
| 2014/0228329 A1* | 8/2014 | Elliott .................. | A61K 31/593 514/167 |

FOREIGN PATENT DOCUMENTS

| | | | | |
|---|---|---|---|---|
| CN | 104814270 | * | 8/2015 | |
| WO | WO-2012078815 A1 | * | 6/2012 | ........... A61K 9/0024 |

* cited by examiner

*Primary Examiner* — Robert A Wax
*Assistant Examiner* — Melissa S Mercier
(74) *Attorney, Agent, or Firm* — Rankin, Hill & Clark LLP

(57) ABSTRACT

This invention provides a 25-OH Vitamin D3 complex, this complex is made of β-cyclodextrin and/or its derivatives and 25-Hydroxy Vitamin D3. This invention also relates to a method of manufacturing this complex of β-cyclodextrin and 25-Hydroxy Vitamin D3, as well as its applications. Due to there being many hydroxy groups at the outside of β-cyclodextrin and/or its derivatives, the complex increases the solubility of entrapped 25-HO Vitamin D3, thus increasing its bioavailability greatly. In addition, the ring structure of β-cyclodextrin protects the unstable unsaturated double bonds of 25-HO Vitamin D3, shield it from oxygen and other harmful chemicals and make it much more stable.

9 Claims, No Drawings

25-HYDROXY VITAMIN D3 COMPLEX AND METHODS OF MANUFACTURE AND ITS APPLICATIONS

TECHNICAL FIELD

This invention relates to a new formulation for 25-Hydroxy Vitamin D3, methods to manufacture the new formulation as well as its application. This invention provides a new complex between 25-Hydroxy Vitamin D3 and β-cyclodextrin and/or its derivatives, such as, methyl-β-cycledextrin, Hydroxypropyl-β-cyclodextrin, that is, some of the hydroxyl group are substituted with methyl, ethyl or propyl groups.

BACKGROUND

25-Hydroxy Vitamin D3 Molecule Structure:

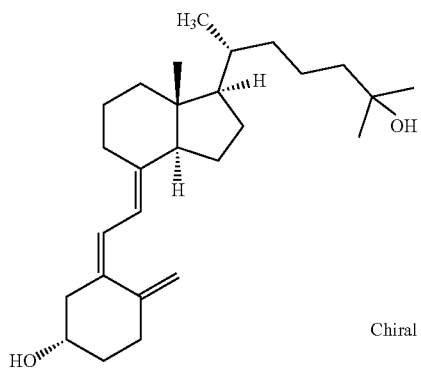 [SMILES: C=C1CC[C@H](O)C/C1=C/C=C1\CCC[C@]2(C)[C@@H]([C@H](C)CCCC(C)(C)O)CC[C@@H]12]

Chemical name: (3b,5Z, 7E)-9,10-Secocholestra-5,7,10(19)-triene-3,25-diol

Due to the unsaturated double bonds at the 5,7,10 positions, it is very easy to be oxidized and degraded, so the market always need a stable formulation to minimize the degradation loss.

Current product on the market is a micro-encapsulation form (U.S. Pat. No. 8,088,410): first, the 25-Hydroxy Vitamin D3 is dissolved in the vegetable oil, add some antioxidant into the oil phase, this is the oil phase. The modified starch is added into the water to make the aqueous phase. Then add the oil phase into aqueous phase while mixing, then this mixture is homogenized to form an emulsion, the 25-Hydroxy Vitamin D3 containing oil was dispersed as tiny oil droplets, with diameter less than 5 um, this emulsion was spray dried to form a fine powder.

There are two problems with current product form, first, since the 25-Hydroxy is dissolved in the oil at molecule level, the starch layer could not stop the oxygen diffusion into the oil phase, it can be oxidized in the air. Its shelf-life is about six month under cold storage condition. When this product exposed to accelerated stability test at 45° C., there is more than 20% loss of active after one week. This add lot of cost to the product for overage and the short shelf-life also add a lot problems for transportation and storage of the product.

The other problem is with its low bioavailability due to the active being dissolved in oil phase, it is not water soluble, it will be absorbed by the small intestine in an animal very slowly, so it cannot be absorbed very well due to the short residence time in the small intestine.

BRIEF DESCRIPTION

The purpose of Invention: toward the two issues with current formulation, after a series of experiments, test and research works, a new formulation was invented for the 25-Hydroxy Vitamin D3, that is, by forming a complex between 25-Hydroxy Vitamin D3 and β-cycledextrin, each 25-Hydroxy Vitamin D3 molecule was enclosed into β-cyclodextrin's cavity, and two β-cycledetrin molecules are needed for each 25-Hydroxy Vitamin D3. Since the unsaturated double bonds was protected in the cavity, its stability was improved, there are many hydroxyl group outside the β-cycledetrin molecule, the complex has higher water solubility, improved its absorption efficiency and bioavailability once it is consumed by animals.

This invention also developed a simple method to produce this new formulation without any special equipments. This invention also developed a method to apply for the new formulation.

Technical Solution: To solve these issues of previous art, a new 25-Hodroxy Vitamin D3 complex was invented, this complex comprises mainly: 25-Hydroxy Vitamin D3 and β-cyclodextrin and/or its derivatives, wherein the complex with mass ration of 6:1~12:1 between β-cyclodextrin and 25-hydroxy Vitamin D3.

wherein the mass ratio of β-cyclodextrin and/or its derivatives and 25-Hydroxy Vitamin D3 is: 6:1~12:1.

wherein the one molecule of 25-Hydroxy Vitamin D3 need two β-cyclodextrin molecule to form the complex.

This invention also provides a method of manufacturing this β-cyclodextrin and 25-hydroxy Vitamin D3 complex, the method comprises the following steps:

1) Adding β-cyclodextrin in to deionized (DI) water, heating it to 45~65° C. while stirring, until dissolved, keeping stirring and maintaining the temperature until next step;

2) Dissolving the 25-Hydroxy Vitamin D3 crystals into an ethanol solution, stirring until dissolved 3) Taking the solution from step 2, adding it into the solution from step 1, slowly and keeping stirring while adding, forming white particles which precipitate out of the solution, continuing to stir while starting to cool the contents to 15-25° C., then filter the precipitate, rinsing and drying to obtain the 25-Hydroxy Vitamin D3 and β-cyclodextrin complex.

Advantageously, in step 1, the mass ratio of DI water and β-cyclodextrin is: 9:1~3:1.

Preferably, in step 2, the mass ratio of 25-Hydrox Vitamin D3 to the volume of ethanol is: 1:4~1:8.

This invention also provides the above mentioned complex, wherein the complex is used in the animal feed application, preferably, wherein the usage of 25-Hydroxy Vitamin D3 and β-cyclodextrin complex is in the range of 0.3 to 0.8 g/MT of feed.

Benefits and advantage of this new formulation: This new invention has several advantages: the complex has better water solubility than 25-Hydroxy Vitamin D3 alone, due to there are several hydroxy groups outside the β-cyclodextrin molecule, this increase its hydrophilic property. So, its adsorption rate and bioavailability is improved dramatically. Also, since the 25-Hydroxy Vitamin D3 was enclosed by β-cyclodextrin into its cavity, isolated out of touch of harmful transition metal, radicals, and oxygen, stomach acid, its stability was improved dramatically too.

DETAILED DESCRIPTION

This invention will be described in more details with below examples. The purpose of these examples is for demonstration only, the nature and scope of this invention will not be limited by these examples.

Example 1

With a 500 ml round bottom flask equipped with stir and jacket for temperature control, first, add 180 g DI water, 20 g of β-cyclodextrin, heat to 45° C. while stirring, until all dissolved. Take 3 gram of 25-Hydroxy Vitamin D3 crystals, dissolved into 12 ml of ethanol in a small glass beaker, stir until all dissolved. Take the solution and slowly add it into the β-cyclodextrin solution while mixing, there are white precipitates formed, fell out of the solution, after all the ethanol solution is added, continue to stir for one hour, filter the solution and rinse with some DI water, dry, get about 21 grams of complex, the HPLC analysis showed it contains 25-Hydroxy Vitamin D3 14 wt %.

Example 2

With a 500 ml round bottom flask equipped with stir and jacket for temperature control, first, add 180 g DI water, add 30 g of β-cyclodextrin, heat to 55° C. while stirring about 15 minutes, get cyclodextrin suspension. Take 3 gram of 25-Hydroxy Vitamin D3 crystals (purity>98 wt %), dissolved into 18 ml of ethanol in a small glass beaker, stir until all dissolved. Take the solution and slowly add it into the cyclodextrin solution while mixing, there are white precipitates formed, fell out of the solution, after all the ethanol solution is added, continue to stir for one hour, filter the solution and rinse with some DI water, dry, get about 22.5 grams of complex, the HPLC analysis showed it contains 25-Hydroxy Vitamin D3 13.8 wt %.

Example 3

500 liter Glass-lined reactor is used for this example, add 180 liter DI water into the reactor, add 35 kg β-cyclodextrin, heat to 65° C., stir for 30 minutes, to get the β-cyclodextrin solution, take 3 kg of 25-Hydroxy Vitamin D3, dissolved into 24 liter of ethanol with a 100 liter glass reactor, and slowly add the solution into the β-cycledextrin solution while mixing, there are white precipitates formed, fell out of the solution, after all the ethanol solution is added, continue to stir for one hour, filter the solution and rinse with some DI water, dry, get about 21.6 kg of complex, the HPLC analysis showed it contains 25-Hydroxy Vitamin D3 13.7 wt %.

Example 4

500 liter Glass-lined reactor is used for this example, add 180 liter DI water into the reactor, add 60 kg β-cyclodextrin, heat to 50° C., stir for 30 minutes, to get the β-cyclodextrin suspension, take 9 kg of 25-Hydroxy Vitamin D3, dissolved into 45 liter of ethanol with a 100 liter glass reactor, and slowly add the solution into the cycledextrin solution while mixing, there are white precipitates formed, fell out of the solution, after all the ethanol solution is added, continue to stir for one hour, filter the solution and rinse with some DI water, dry, get about 63.6 kg of complex, the HPLC analysis showed it contains 25-Hydroxy Vitamin D3 13.8 wt %.

Experimental Examples 1 Thermal Stability Test

Thermal stability tests for the complex generated in the example 1-4. The complex is more concentrated than the product on the market, it need to be diluted with diluent, such as, modified starch, starch, maltodextrin, lactose, etc.

Take one gram complex mix with 9 gram of lactose, mix well, test it thermal stability along with DSM Rovimix HyD sample. The oven temperature is set at 45° C. Take sample and analysis its 25-Hydroxy vitamin D3 content every week. Below table listed the results:

| content, wt % (25-OHVD3) | week 0 | Week 1 | Week 2 | Week3 | Week4 |
|---|---|---|---|---|---|
| Complex from EX1 | 1.40 | 1.37 | 1.38 | 1.36 | 1.35 |
| Complex from EX2 | 1.38 | 1.36 | 1.37 | 1.36 | 1.34 |
| Complex from EX3 | 1.37 | 1.35 | 1.36 | 1.36 | 1.35 |
| Complex from EX4 | 1.38 | 1.36 | 1.37 | 1.36 | 1.34 |
| Rovimix HyD | 1.38 | 1.29 | 1.21 | 1.13 | 1.04 |

These results showed that, the content of 25-OH-VD3 in the complex of beta-cyclodextrin and 25-OH-VD3 did not change much, about 3%, while the current micro-encapsulated product on the market loss about 25%.

Experimental Examples 2 Bio-Efficiency Tests

Three group of chicken used in the test, the blood was drawn from the chicken one week after feed started, group A as control, with no Vitamin D3 added, the 25-Hydroxy VD3 in the blood is very low, the group B is fed with feed contain 50 μg/kg 25-Hydroxy VD3 (from Rovimix HyD); the group C is fed with feed contain 50 μg/kg 25-Hydroxy VD3 (from 25-Hydroxy VD3 and β-cyclodextrin complex made at example 1).

| Content, ng/ml | 1 week | 2 week | 3 week | 4 week | 5 week |
|---|---|---|---|---|---|
| Group A | <10 | <10 | <10 | <10 | <10 |
| Group C | 65 | 64 | 68 | 66 | 67 |
| Group B | 55 | 53 | 56 | 55 | 54 |

These results showed that, at the same level of 25-Hydroxy VD3 feed, this new product can increase 20% higher of 25-Hydroxy VD3 in the blood than other product, it is more bioavailable than in known product.

Above mentioned are preferred steps or method to utilize this invention, but, for the technical people in these fields, utilizing the principle of this invention, there are many modifications that can be made to alter, improve it, all these changes and improvements fall within the scope of the present invention as defined in the appended Claims.

The invention claimed is:

1. A 25-Hydroxy Vitamin D3 complex, characterized in that, it comprises β-cyclodextrin and 25-hydroxy Vitamin D3,
   wherein the complex includes 25-hydroxy Vitamin D3 molecules encapsulated within β-cyclodextrin molecules and wherein the mass ratio of β-cyclodextrin and 25-hydroxy Vitamin D3 is: 6:1 to 12:1.

2. The complex of claim 1, characterized by comprising two β-cyclodextrin molecules for one molecule of 25-Hydroxy Vitamin D3 to form the complex.

3. A method of manufacturing the 25-Hydroxy Vitamin D3 and β-cyclodextrin and complex of claim 1, the method being characterized by the following steps:
   1) Adding β-cyclodextrin into deionized (DI) water, heating to 45° C. while stirring, until dissolved, keeping stirring and holding the temperature until next step;

2) Dissolving the 25-Hydroxy Vitamin D3 crystals into an ethanol solution, stirring until dissolved;

3) Taking the solution from step 2, adding it into the aqueous solution from step 1, slowly and stirring while adding, thereby forming white particles which precipitate out of the solution; continuing to stir while starting to cool the contents to 15-25° C.; then filtering out the precipitate; rinsing and drying to obtain the 25-Hydroxy Vitamin D3 and β-cyclodextrin complex.

4. The method of claim 3, wherein in step 1, the mass ratio of deionized water (DI) water and β-cyclodextrin is: 9:1~3:1.

5. The method of claim 3, wherein in step 2, the mass ratio of 25-Hydroxy Vitamin D3 to the volume of ethanol is: 1:4~1:8.

6. An animal feed including the 25-Hydroxy Vitamin D3 and β-cyclodextrin complex of claim 1.

7. The animal feed of claim 6, wherein the usage of the 25-Hydroxy Vitamin D3 and β-cyclodextrin complex is in the range of 0.3 to 0.8 g/MT of feed.

8. The method of claim 3, wherein the 25-hydroxy Vitamin D3 molecules are each encapsulated by two β-cyclodextrin molecules.

9. The animal feed of claim 6, wherein the 25-hydroxy Vitamin D3 molecules are each encapsulated by two β-cyclodextrin molecules.

* * * * *